(12) United States Patent
Yu et al.

(10) Patent No.: US 10,601,069 B2
(45) Date of Patent: Mar. 24, 2020

(54) NON-AQUEOUS ELECTROLYTE ADDITIVE, AND NON-AQUEOUS ELECTROLYTE FOR LITHIUM SECONDARY BATTERY COMPRISING THE SAME AND LITHIUM SECONDARY BATTERY

(71) Applicant: LG Chem, Ltd., Seoul (KR)

(72) Inventors: Sung Hoon Yu, Daejeon (KR); Kyung Mi Lee, Daejeon (KR)

(73) Assignee: LG Chem, Ltd. (KR)

(*) Notice: Subject to any disclaimer, the term of this patent is extended or adjusted under 35 U.S.C. 154(b) by 179 days.

(21) Appl. No.: 15/737,503

(22) PCT Filed: Mar. 21, 2017

(86) PCT No.: PCT/KR2017/003032
§ 371 (c)(1),
(2) Date: Dec. 18, 2017

(87) PCT Pub. No.: WO2017/164625
PCT Pub. Date: Sep. 28, 2017

(65) Prior Publication Data
US 2018/0198157 A1  Jul. 12, 2018

(30) Foreign Application Priority Data

Mar. 23, 2016 (KR) .......... 10-2016-0034809
Apr. 25, 2016 (KR) .......... 10-2016-0049963
Mar. 20, 2017 (KR) .......... 10-2017-0034826

(51) Int. Cl.
| | |
|---|---|
| *H01M 10/052* | (2010.01) |
| *H01M 10/0525* | (2010.01) |
| *H01M 10/0567* | (2010.01) |
| *C07D 213/84* | (2006.01) |
| *C07D 213/85* | (2006.01) |
| *C07C 255/25* | (2006.01) |
| *C07C 255/19* | (2006.01) |
| *C07C 255/09* | (2006.01) |
| *C07D 241/24* | (2006.01) |
| *C07C 255/54* | (2006.01) |
| *C07C 255/15* | (2006.01) |
| *C07C 255/13* | (2006.01) |
| *C07C 255/24* | (2006.01) |
| *C07C 255/07* | (2006.01) |
| *C07C 255/51* | (2006.01) |
| *H01M 2/16* | (2006.01) |
| *H01M 4/131* | (2010.01) |

(Continued)

(52) U.S. Cl.
CPC ....... *H01M 10/0525* (2013.01); *C07C 255/07* (2013.01); *C07C 255/09* (2013.01); *C07C 255/13* (2013.01); *C07C 255/15* (2013.01); *C07C 255/19* (2013.01); *C07C 255/24* (2013.01); *C07C 255/25* (2013.01); *C07C 255/51* (2013.01); *C07C 255/54* (2013.01); *C07D 213/84* (2013.01); *C07D 213/85* (2013.01); *C07D 241/24* (2013.01); *H01M 2/1673* (2013.01); *H01M 4/131* (2013.01); *H01M 4/662* (2013.01); *H01M 10/052* (2013.01); *H01M 10/0567* (2013.01); *H01M 10/0585* (2013.01); *H01M 10/0568* (2013.01); *H01M 10/0569* (2013.01); *H01M 2004/027* (2013.01); *H01M 2004/028* (2013.01); *H01M 2300/0025* (2013.01); *H01M 2300/0034* (2013.01)

(58) Field of Classification Search
CPC ... C07C 255/07; C07C 255/09; C07C 255/13; C07C 255/15; C07C 255/19; C07C 255/24; C07C 255/25; C07C 255/51; C07C 255/54; C07D 213/84; C07D 213/85; C07D 241/24; H01M 4/131; H01M 4/662; H01M 10/052; H01M 10/0525; H01M 10/0567; H01M 10/0565; H01M 10/0569; H01M 10/0585
USPC .................................................. 429/231.95
See application file for complete search history.

(56) References Cited

U.S. PATENT DOCUMENTS 4,544,615 A * 10/1985 Shishikura ............ H01M 10/05
429/199
2012/0171581 A1  7/2012 Abe et al.
(Continued)

FOREIGN PATENT DOCUMENTS

KR  20120062776 A  6/2012
KR  20120111272 A  10/2012
(Continued)

OTHER PUBLICATIONS

Remizova et al, Cyanoethylation of Acetylenic Amines, Zhurnal Organichskoi Khimii, vol. 8, Issue 6, 1143-1146(1972). (Year: 1972).*

(Continued)

*Primary Examiner* — Amanda C. Walke
(74) *Attorney, Agent, or Firm* — Lerner, David, Littenberg, Krumholz & Mentlik, LLP

(57) ABSTRACT

The present invention relates to a non-aqueous electrolyte additive, and a non-aqueous electrolyte for a lithium secondary battery including the same and a lithium secondary battery, and particularly, to a non-aqueous electrolyte additive having a nitrile group and a propargyl group, and a non-aqueous electrolyte for a lithium secondary battery and a lithium secondary battery, which include the non-aqueous electrolyte additive so that capacity and cycle lifespan characteristics at high temperature can be improved.

9 Claims, No Drawings

(51) Int. Cl.
   *H01M 4/66*   (2006.01)
   *H01M 10/0585*   (2010.01)
   *H01M 10/0569*   (2010.01)
   *H01M 10/0568*   (2010.01)
   *H01M 4/02*   (2006.01)

(56) References Cited

U.S. PATENT DOCUMENTS

| | | |
|---|---|---|
| 2013/0316252 A1 | 11/2013 | Lee et al. |
| 2013/0330582 A1 | 12/2013 | Ihara et al. |
| 2014/0322596 A1 | 10/2014 | Shatunov et al. |
| 2015/0194703 A1 | 7/2015 | Suguro et al. |

FOREIGN PATENT DOCUMENTS

| | | |
|---|---|---|
| KR | 101278692 B1 | 6/2013 |
| KR | 20130130465 A | 12/2013 |
| KR | 20140127741 A | 11/2014 |
| WO | 2014007026 A1 | 1/2014 |

OTHER PUBLICATIONS

Machine translation of KR 10-2012-0062776 (no date).*
Machine translation of KR 10-2012-0111272 (no date).*
Ma et al, Highly Conductive Electrolytes Derived from Nitrile Solvents, Journal of the Electrochemical Society, 162, (7), A1276-1281 (2015). (Year: 2015).*
Extended European Search Report including Written Opinion for Application EP17770595.1 dated Jun. 5, 2018.
Lingam V.S. Prasada et al., "A simple approach to highly functionalized benzo[b]furans from phenols and aryl iodides via aryl propargyl ethers", Tetrahedron Letters, Elsevier, Jun. 30, 2008, vol. 49, No. 27, pp. 4260-4264, XP022695657.
Yunus Zorlu et al., "Phthalonitriles Functionalized for Click Chemistry. Design, Synthesis and Structural Characterization", Journal of Chemical Crystallography, Dec. 1, 2013, vol. 43, No. 12, pp. 636-645, XP055477706.
Search report from International Applicaiton No. PCT/KR2017/003032, dated Jun. 23, 2017.

* cited by examiner

NON-AQUEOUS ELECTROLYTE ADDITIVE, AND NON-AQUEOUS ELECTROLYTE FOR LITHIUM SECONDARY BATTERY COMPRISING THE SAME AND LITHIUM SECONDARY BATTERY

CROSS-REFERENCE TO RELATED APPLICATION

This application is a national phase entry under 35 U.S.C. § 371 of International Patent Application No. PCT/KR2017/003032, filed Mar. 21, 2017, which claims priority to and the benefit of Korean Patent Application No. 10-2016-0034809, filed on Mar. 23, 2016, Korean Patent Application No. 10-2016-0049963, filed on Apr. 25, 2016, and Korean Patent Application No. 10-2017-0034826, filed on Mar. 20, 2017, the disclosures of which are incorporated herein by reference in their entirety.

TECHNICAL FIELD

The present invention relates to a non-aqueous electrolyte additive, and a non-aqueous electrolyte for a lithium secondary battery comprising the same and a lithium secondary battery, and particularly, to a non-aqueous electrolyte additive capable of improving capacity and cycle lifespan characteristics when stored at high temperature, and a non-aqueous electrolyte for a lithium secondary battery including the same and a lithium secondary battery including the same.

BACKGROUND ART

As electronic devices become smaller, lighter, thinner, and more portable with the development of the information and communication industry, there is a growing demand for increasing the energy density of batteries used as a power source for such electronic devices.

A lithium battery, particularly, a lithium ion battery (LIB) is the battery which can best satisfy the above demand, and has been employed as a power source for various portable devices due to high energy density and simple design.

Recently, as use of lithium secondary batteries has been expanding from conventional small-sized electronic devices to large-sized electronic devices, automobiles, smart grids, and the like, a lithium secondary battery capable of maintaining excellent performance not only at room temperature but also even in harsher environments such as high or low temperature environments is required.

A lithium ion secondary battery is composed of a negative electrode made of a carbon-based material which can occlude and release lithium ions, a positive electrode made of a lithium-containing transition metal oxide, and a non-aqueous electrolyte. In a lithium ion secondary battery, lithium ions eluted from a positive electrode active material are intercalated into a negative electrode active material such as a carbon particle through $1^{st}$ charging and the lithium ions are deintercalated through discharging. As lithium ions reciprocate between opposite electrodes as such, they transfer energy. Therefore, a secondary battery can be charged and discharged.

However, as the charging and discharging of a lithium ion secondary battery proceed, the structure of a positive electrode active material is destroyed, and thus performance of a positive electrode is degraded. Also, when the structure of a positive electrode is destroyed, metal ions eluted from a surface of the positive electrode are electrodeposited on a negative electrode, and thus the negative electrode is deteriorated. Such a deterioration of battery performance tends to be further accelerated when the potential of a positive electrode increases or a battery is exposed to high temperature.

Accordingly, there is a need to develop a positive electrode, an electrolyte, or the like having novel components which can solve the above problems.

PRIOR-ART DOCUMENTS

Korean Registered Patent No. 10-1278692
Korean Patent Application Publication No. 10-2014-0127741

DISCLOSURE

Technical Problem

The present invention is designed to solve the problems of the prior art, and it is an aspect of the present invention to provide a non-aqueous electrolyte additive which exhibits an excellent effect of adsorbing metal ions eluted from a positive electrode.

In addition, it is another aspect of the present invention to provide a non-aqueous electrolyte for a lithium secondary battery comprising the non-aqueous electrolyte additive.

Additionally, it is still another aspect of the present invention to provide a lithium secondary battery which includes the non-aqueous electrolyte for a lithium secondary battery so that performance in various aspects is improved.

Technical Solution

In order to accomplish the above objectives, according to an embodiment of the present invention, there is provided a non-aqueous electrolyte additive which includes at least one compound selected from the group consisting of compounds represented by Formula I and Formula II below:

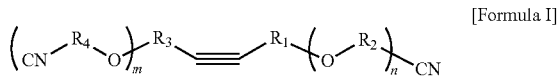

[Formula I]

In Formula I, $R_1$ is a $C_1$ to $C_5$ linear or nonlinear alkylene group substituted or unsubstituted with at least one nitrile group, or a $C_6$ to $C_8$ aromatic group substituted or unsubstituted with at least one nitrile group, $R_2$ is a $C_1$ to $C_5$ linear or nonlinear alkylene group substituted or unsubstituted with at least one nitrile group, a $C_6$ to $C_8$ aromatic group substituted or unsubstituted with at least one nitrile group, a $C_6$ to $C_8$ heteroaromatic group substituted or unsubstituted with at least one nitrile group, a $C_2$ to $C_5$ linear or nonlinear alkenyl group, or —C(O)—$R_9$—, wherein $R_9$ is a $C_1$ to $C_3$ linear or nonlinear alkylene group substituted or unsubstituted with at least one nitrile group, $R_3$ is hydrogen or a $C_1$ to $C_5$ linear or nonlinear alkyl group substituted or unsubstituted with at least one nitrile group when m is 0, and a $C_1$ to $C_5$ linear or nonlinear alkylene group when m is 1, $R_4$ is a $C_1$ to $C_3$ alkylene group or —$R_{10}$—C(O)—, wherein $R_{10}$ is a $C_1$ to $C_3$ alkylene group, and n and m each independently are an integer of 0 or 1.

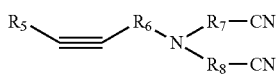
[Formula II]

In Formula II,
$R_5$ is hydrogen or a $C_1$ to $C_5$ linear or nonlinear alkyl group substituted or unsubstituted with at least one nitrile group, and $R_6$ to $R_8$ each independently are a $C_1$ to $C_5$ linear or nonlinear alkylene group.

In addition, according to another embodiment of the present invention, there is provided a non-aqueous electrolyte for a lithium secondary battery, which includes an ionizable lithium salt; an organic solvent; and the non-aqueous electrolyte additive according to the present invention.

The non-aqueous electrolyte additive may be included at 0.5 wt % to 5 wt %, particularly 1 wt % to 5 wt %, based on the total content of the non-aqueous electrolyte.

Additionally, according to still another embodiment of the present invention, there is provided a lithium secondary battery which includes a negative electrode, a positive electrode, a separator interposed between the negative electrode and the positive electrode, and the non-aqueous electrolyte according to the present invention.

Advantageous Effects

According to an embodiment of the present invention, a non-aqueous electrolyte can be prepared which includes a non-aqueous electrolyte additive that is capable of combining with metal ions eluted from a positive electrode upon charging and discharging and metal impurities mixed in a preparation process to form a complex, and thus is capable of suppressing electrodeposition of metal ions on a surface of a negative electrode and forming a more stable ionic conductive film on surfaces of a negative electrode and a positive electrode. Further, a lithium secondary battery can be manufactured which includes the non-aqueous electrolyte and thus exhibits an improvement in performance in various aspects such as capacity characteristics, cycle lifespan characteristics, and the like when stored at high temperature.

MODE OF THE INVENTION

Hereinafter, the present invention will be described in more detail.

Terms and words used in this specification and claims should not be interpreted as limited to commonly used meanings or meanings in dictionaries and should be interpreted with meanings and concepts which are consistent with the technological scope of the invention based on the principle that the inventors have appropriately defined concepts of terms in order to describe the invention in the best way.

In a lithium secondary battery among electrochemical devices, a kind of passivation film is formed by electrochemical oxidative decomposition of an electrolyte at a positive electrode of the battery, particularly at a position where surface bonding is present or at an activated position, and this passivation film increases impedance with respect to co-intercalation of lithium ions into a positive electrode active material. Also, when the battery is overcharged or stored at high temperature, an excessive amount of lithium ions is released from a positive electrode, and thus structural destruction of a positive electrode active material or chemical dissolution caused by an electrolyte occurs, thereby ions of Co, Mn, Ni, and the like are eluted from a positive electrode active material. These reactions result in degradation of the performance of a positive electrode itself, and also cause side reactions of an electrolyte and structural destruction of a negative electrode to degrade performance in various aspects of a secondary battery.

In the present invention, there is provided a non-aqueous electrolyte additive which includes at least one nitrile group and a propargyl group having performance of adsorbing metal ions in a structure, and thus is capable of suppressing generation of metal ions inside of a battery.

In addition, in the present invention, there is provided a non-aqueous electrolyte for a lithium secondary battery, which includes the non-aqueous electrolyte additive, and thus side reactions are decreased.

Additionally, in the present invention, there is provided a lithium secondary battery which includes the non-aqueous electrolyte for a lithium secondary battery, and thus exhibits an improvement in performance in various aspects such as capacity characteristics, cycle lifespan characteristics, and the like when stored at high temperature.

Specifically, according to an embodiment of the present invention, there is provided a non-aqueous electrolyte additive which includes at least one compound selected from the group consisting of compounds represented by Formula I and Formula II below.

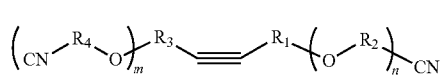
[Formula I]

In Formula I,
$R_1$ is a $C_1$ to $C_5$ linear or nonlinear alkylene group substituted or unsubstituted with at least one nitrile group, or a $C_6$ to $C_8$ aromatic group substituted or unsubstituted with at least one nitrile group, $R_2$ is a $C_1$ to $C_5$ linear or nonlinear alkylene group substituted or unsubstituted with at least one nitrile group, a $C_6$ to $C_8$ aromatic group substituted or unsubstituted with at least one nitrile group, a $C_6$ to $C_8$ heteroaromatic group substituted or unsubstituted with at least one nitrile group, a $C_2$ to $C_5$ linear or nonlinear alkenyl group, or —C(O)—$R_9$—, wherein $R_9$ is a $C_1$ to $C_3$ linear or nonlinear alkylene group substituted or unsubstituted with at least one nitrile group, $R_3$ is hydrogen or a $C_1$ to $C_5$ linear or nonlinear alkyl group substituted or unsubstituted with at least one nitrile group when m is 0, and a $C_1$ to $C_5$ linear or nonlinear alkylene group when m is 1, $R_4$ is a $C_1$ to $C_3$ alkylene group or —$R_{10}$—C(O)—, wherein $R_{10}$ is a C1 to C3 alkylene group, and n and m each independently are an integer of 0 or 1.

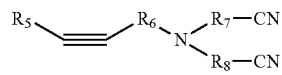
[Formula II]

In Formula II,
$R_5$ is hydrogen or a C1 to C5 linear or nonlinear alkyl group substituted or unsubstituted with at least one nitrile group, and $R_6$ to $R_8$ each independently are a C1 to C5 linear or nonlinear alkylene group.

Specific examples of the compound represented by Formula I include at least one compound selected from the group consisting of compounds represented by Formulas I-1 to 1-39 below.

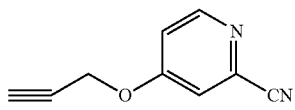
(Formula I-1)
CAS No.: 1340327-98-1, Mw: 158.16

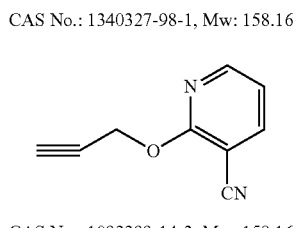
(Formula I-2)
CAS No.: 1092299-14-3, Mw: 158.16

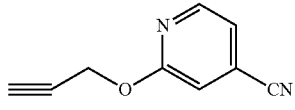
(Formula I-3)
CAS No.: 1092299-10-9, Mw: 158.16

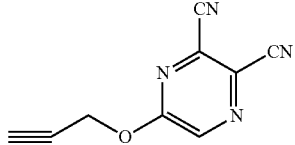
(Formula I-4)
CAS No.: 77858-71-0, Mw: 184.15

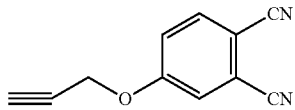
(Formula I-5)
CAS No.: 119088-71-1, Mw: 182.18

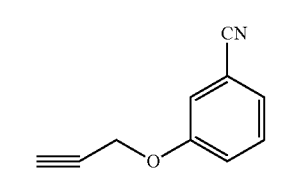
(Formula I-6)
CAS No.: 237748-26-4, Mw: 157.17

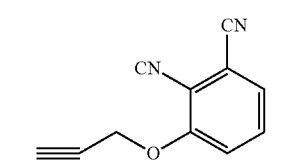
(Formula I-7)
CAS No.: 181016-27-3, Mw: 182.18

-continued

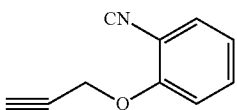
(Formula I-8)
CAS No.: 65211-56-5, Mw: 157.17

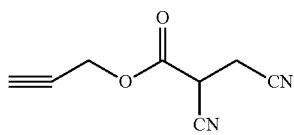
(Formula I-9)
CAS No.: 477776-32-2, Mw: 162.15

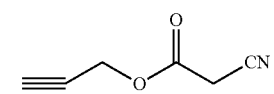
(Formula I-10)
CAS No.: 30764-61-5, Mw: 123.11

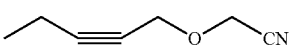
(Formula I-11)
CAS No.: 130772584-3, Mw: 123.15

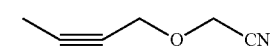
(Formula I-12)
CAS No.: 1226870-15-0, Mw: 109.13

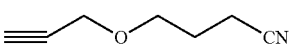
(Formula I-13)
CAS No.: 1152602-85-1, Mw: 123.15

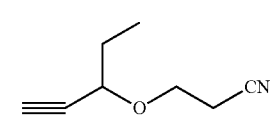
(Formula I-14)
CAS No.: 875231-41-7, Mw: 137.18

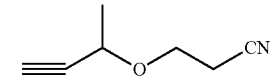
(Formula I-15)
CAS No.: 874488-13-8, Mw: 123.15

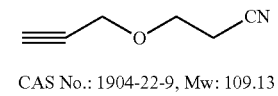
(Formula I-16)
CAS No.: 1904-22-9, Mw: 109.13

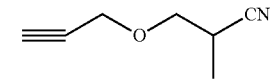
(Formula I-17)
CAS No.: 135180-11-9, Mw: 123.15

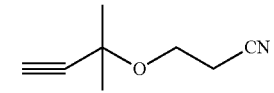
(Formula I-18)
CAS No.: 15496-08-9, Mw: 137.18

(Formula I-19)
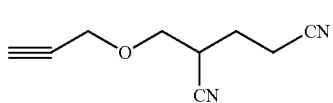
CAS No.: 135180-12-0, Mw: 162.19

(Formula I-20)
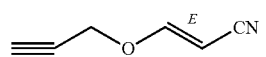
CAS No.: 552335-84-9, Mw: 107.11

(Formula I-21)
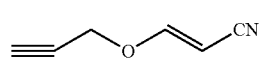
CAS No.: 30908-62-4, Mw: 107.11

(Formula I-22)
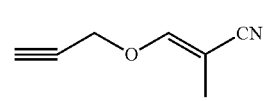
CAS No.: 70013-05-7, Mw: 121.14

(Formula I-23)
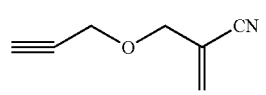
CAS No.: 60838-53-1, Mw: 121.14

(Formula I-24)
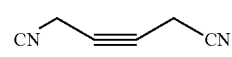
CAS No.: 1403752-26-0, Mw: 104.11

(Formula I-25)
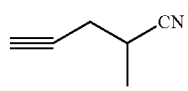
CAS No.: 1231244-87-3, Mw: 93.13

(Formula I-26)
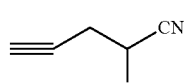
CAS No.: 130575-28-9, Mw: 104.11

(Formula I-27)
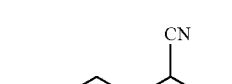
CAS No.: 106814-29-3, Mw: 118.14

(Formula I-28)
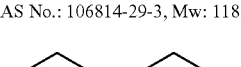
CAS No.: 93604-63-8, Mw: 93.13

(Formula I-29)
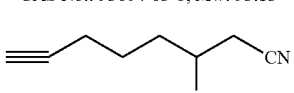
CAS No.: 78790-62-2, Mw: 146.19

(Formula I-30)
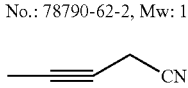
CAS No.: 19754-82-6, Mw: 79.10

(Formula I-31)
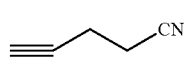
CAS No.: 15956-07-7, Mw: 79.10

(Formula I-32)
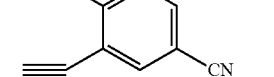
CAS No.: 18719-29-4, Mw: 93.13

(Formula I-33)
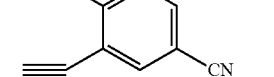
CAS No.: 14918-21-9, Mw: 93.13

(Formula I-34)
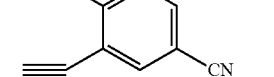
CAS No.: 6926-20-1, Mw: 118.14

(Formula I-35)
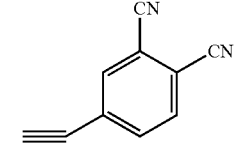
CAS No.: 1187569-59-0, Mw: 152.15

(Formula I-36)
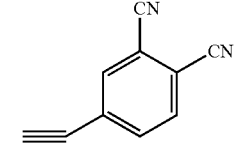
CAS No.: 99276-98-9, Mw: 152.15

(Formula I-37)
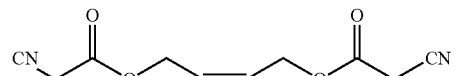
CAS No.: 1142329-71-2, Mw: 220.18

(Formula I-38)
CAS No.: 6095-08-5, Mw: 220.27

(Formula I-39)
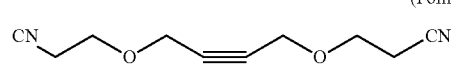
CAS No.: 90918-31-3, Mw: 192.21

In addition, specific examples of the compound represented by Formula II include at least one compound selected from the group consisting of compounds represented by Formulas II-1 to II-4 below.

(Formula II-1)
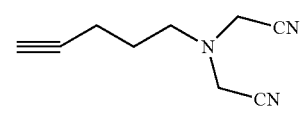
CAS No.: 1566708-82-4, Mw: 161.20

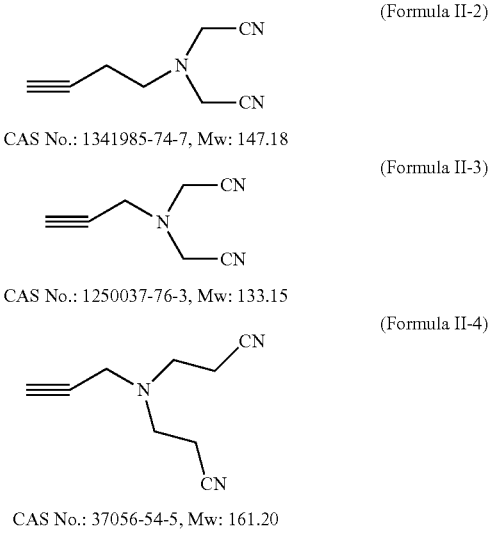

(Formula II-2)
CAS No.: 1341985-74-7, Mw: 147.18

(Formula II-3)
CAS No.: 1250037-76-3, Mw: 133.15

(Formula II-4)
CAS No.: 37056-54-5, Mw: 161.20

A polar nitrile group (i.e., a cyano group) having high dipole moment included in the compounds represented by Formula I or II easily adsorbs metal ions of Co, Mn, or Ni eluted from a positive electrode due to chemical dissolution caused by an electrolyte in a repetitive charging and discharging process of a battery, or metal impurities mixed upon a raw material or a preparation process. In addition to the adsorption of metal ions, generation of HF caused by decomposition of a salt is suppressed since unshared electrons of N in the nitrile group stabilize an anion of a salt, and particularly, the nitrile group combines more strongly with a surface of a positive electrode at high temperature to form a complex structure or a ligand, and thus a stable ionic conductive film may be formed on a surface of a positive electrode. Therefore, precipitation of some eluted transition metals on a negative electrode is prevented upon storage at high temperature, several side reactions between an electrolyte and a positive electrode and generation of gas are also suppressed by forming a stable film on a surface of a positive electrode, and thus a battery swelling phenomenon is prevented. As a result, high-temperature storage characteristics such as residual capacity and recovery capacity upon storage at high temperature may be further improved.

In addition, a propargyl group with a triple bond included in the compounds represented by Formula I or II is known to have performance of adsorbing metal ions, and thus may combine with other metal impurities which do not combine with the nitrile group to form a complex to form an additional complex. Furthermore, since the propargyl group may be reduced on a surface of a negative electrode to form a stable ionic conductive film on a surface of a negative electrode, lithium ions are smoothly occluded and released from a negative electrode upon storage at high temperature, thereby lifespan characteristics of a secondary battery may be improved.

Meanwhile, compared to compounds in which one end of a triple bond includes hydrogen or short substituents, in the case of compounds represented by Formulas I-24 and I-37 to I-39 in which both sides of a triple bond symmetrically combine with long substituents, a generated polymerization film is relatively thicker and resistance is higher, and thus, relatively, cycle capacity retention (%) is slightly degraded. On the other hand, voltage after storage at high temperature may be relatively high due to a more excellent effect of adsorbing metal impurities.

As described above, in the present invention, since at least one compound of compounds represented by Formula I or II including two functional groups such as a nitrile group and a propargyl group is used as a non-aqueous electrolyte additive, the non-aqueous electrolyte additive combines with metal ions eluted from a positive electrode upon charging and discharging and/or metal impurities mixed in a preparation process to form a complex, and thus electrodeposition of metal ions on a surface of a negative electrode may be suppressed and a more stable ionic conductive film may be formed on surfaces of electrodes. Therefore, a secondary battery may be manufactured which exhibits an improvement in performance in various aspects such as capacity characteristics, cycle lifespan characteristics, and the like when stored at high temperature.

In addition, according to another embodiment of the present invention, there is provided a non-aqueous electrolyte for a lithium secondary battery, which includes an ionizable lithium salt; an organic solvent; and the non-aqueous electrolyte additive.

The non-aqueous electrolyte additive may be included at about 0.5 wt % to 5 wt %, particularly 1 wt % to 5 wt %, based on the total weight of the non-aqueous electrolyte. When a content of the additive is less than 0.5 wt %, the effects, to be described below, of suppressing elution of metal ions and improving capacity characteristics upon storage at high temperature may be insignificant. When a content of the additive is greater than 5 wt %, capacity of a battery may be decreased and viscosity of an electrolyte may be increased due to side reactions of a excess non-aqueous electrolyte additive, and thus an increase in resistance and a decrease in ionic conductivity may occur and performance in various aspects of a secondary battery may be degraded.

In an embodiment, the lithium salt included in the non-aqueous electrolyte according to the present invention may be, without limitation, a lithium salt commonly used in an electrolyte for a lithium secondary battery. For example, the lithium salt includes $Li^+$ as a cation and at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3$ $CF_2SO_3^-$, $(CF_3SO_2)_2N^-$, $(F_2SO_2)_2N^-$, $CF_3$ $CF_2(CF_3)_2$ $CO^-$, $(CF_3SO_2)_2$ $CH^-$, $CF_3(CF_2)_7SO_3^-$, $CF_3$ $CO_2^-$, $CH_3$ $CO_2^-$, $SCN^-$, and $(CF_3$ $CF_2SO_2)_2N^-$, as an anion. Also, the lithium salt may be one or a mixture of two or more thereof as necessary. Although the lithium salt may be appropriately adjusted to be within a usable range, it may be included at a concentration of 0.8 M to 1.5 M in an electrolyte to accomplish an effect of forming an optimum film for preventing an electrode surface from being corroded.

In addition, the organic solvent included in the non-aqueous electrolyte according to the present invention may be a solvent commonly used in an electrolyte for a lithium secondary battery without limitation. For example, the organic solvent may include any one or a mixture of two or more of an ether compound, an ester compound, an amide compound, a linear carbonate compound, a cyclic carbonate compound, and the like.

Among these, a cyclic carbonate compound, a linear carbonate compound, or a mixture thereof may be typically included. Specific examples of the cyclic carbonate compound include any one or a mixture of two or more selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC). Also, specific examples of the linear carbonate compound include any one or a mixture of two or more selected from the group consisting of dimethyl carbonate (DMC), diethyl carbonate (DEC), dipropyl carbonate, ethyl methyl carbonate (EMC), methyl propyl carbonate, and ethyl propyl carbonate, but the present invention is not limited thereto.

In particular, ethylene carbonate and propylene carbonate, which are cyclic carbonate compounds among the carbonate-based organic solvents, are high-viscosity organic solvents and are preferably used because they dissociate a lithium salt in an electrolyte effectively due to their high dielectric constant. It is preferable that such a cyclic carbonate compound is used in combination with the linear carbonate compound having low viscosity and a low dielectric constant such as dimethyl carbonate and diethyl carbonate in an appropriate ratio so that an electrolyte having high electrical conductivity may be formed.

In addition, the ether compound among the organic solvents may be any one or a mixture of two or more selected from the group consisting of dimethyl ether, diethyl ether, dipropyl ether, methyl ethyl ether, methyl propyl ether, and ethyl propyl ether, but the present invention is not limited thereto.

Additionally, the ester compound among the organic solvents may be any one or a mixture of two or more selected from the group consisting of a linear ester such as methyl acetate, ethyl acetate, propyl acetate, methyl propionate, ethyl propionate, propyl propionate, and butyl propionate; and a cyclic ester such as γ-butyrolactone, γ-valerolactone, γ-caprolactone, σ-valerolactone, and ε-caprolactone, but the present invention is not limited thereto.

The non-aqueous electrolyte according to the present invention may further include an additive for forming a SEI film as necessary. As an additive for forming a SEI film that may be used in the present invention, any one or a mixture of two or more of vinylene carbonate, vinyl ethylene carbonate, fluoroethylene carbonate, cyclic sulfite, saturated sultone, unsaturated sultone, non-cyclic sulfone, and the like may be used.

In this case, the cyclic sulfite may be ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite, 1,3-butylene glycol sulfite, or the like. The saturated sultone may be 1,3-propane sultone, 1,4-butane sultone, or the like. The unsaturated sultone may be ethane sultone, 1,3-propene sultone, 1,4-butene sultone, 1-methyl-1,3-propene sultone, or the like. The non-cyclic sulfone may be divinyl sulfone, dimethyl sulfone, diethyl sulfone, methyl ethyl sulfone, methyl vinyl sulfone, or the like.

In addition, according to still another embodiment of the present invention, there is provided a lithium secondary battery which includes a positive electrode, a negative electrode, a separator interposed between the positive electrode and the negative electrode, and a non-aqueous electrolyte which is the non-aqueous electrolyte according to the present invention.

Specifically, the lithium secondary battery according to the present invention may be manufactured by injecting the non-aqueous electrolyte according to the present invention into an electrode assembly composed of the positive electrode, the negative electrode, and the separator interposed between the positive electrode and the negative electrode. Here, the positive electrode, the negative electrode, and the separator, which constitute the electrode assembly, may be materials commonly used in manufacturing a lithium secondary battery.

In this case, the positive electrode may be manufactured by forming a positive electrode mixture layer on a positive electrode current collector.

The positive electrode mixture layer may be formed by applying a positive electrode slurry including a positive electrode active material, a binder, a conductive material, a solvent, and the like, followed by drying and rolling.

The positive electrode current collector is not particularly limited as long as it does not cause a chemical change in the battery and has conductivity. For example, stainless steel, aluminum, nickel, titanium, calcined carbon, or aluminum or stainless steel whose surface is treated with carbon, nickel, titanium, silver, or the like may be used as the positive electrode current collector.

The positive electrode active material may be a compound capable of reversible intercalation and deintercalation of lithium ions, and particularly, may include a lithium composite metal oxide containing lithium and one or more metals such as cobalt, manganese, nickel, or aluminum. More particularly, the lithium composite metal oxide may be any one or a mixture of two or more of lithium-manganese-based oxides (e.g., $LiMnO_2$, $LiMn_2O_4$ or the like), lithium-cobalt-based oxides (e.g., $LiCoO_2$ or the like), lithium-nickel-based oxides (e.g., $LiNiO_2$ or the like), lithium-nickel-manganese-based oxides (e.g., $LiNi_{1-Y}Mn_YO_2$ (here, $0<Y<1$), $LiMn_{2-Z}Ni_ZO_4$ (here, $0<Z<2$) or the like), lithium-nickel-cobalt-based oxides (e.g., $LiNi_{1-Y1}Co_{Y1}O_2$ (here, $0<Y1<1$) or the like), lithium-manganese-cobalt-based oxides (e.g., $LiCo_{1-Y2}Mn_{Y2}O_2$ (here, $0<Y2<1$), $LiMn_{2-Z1}Co_{Z1}O_4$ (here, $0<Z1<2$) or the like), lithium-nickel-manganese-cobalt-based oxides (e.g., $Li(Ni_pCo_qMn_{r1})O_2$ (here, $0<p<1$, $0<q<1$, $0<r1<1$, and $p+q+r1=1$), $Li(Ni_{p1}Co_{q1}Mn_{r2})O_4$ (here, $0<p1<2$, $0<q1<2$, $0<r2<2$, and $p1+q1+r2=2$), or the like), or lithium-nickel-cobalt-transition metal (M) oxides (e.g., $Li(Ni_{p2}Co_{q2}Mn_{r3}M_{s2})O_2$(here, M is selected from the group consisting of Al, Fe, V, Cr, Ti, Ta, Mg, and Mo, and p2, q2, r3, and s2 represent a atomic fraction of each independent element, and satisfy $0<p2<1$, $0<q2<1$, $0<r3<1$, $0<s2<1$, and $p2+q2+r3+s2=1$) or the like). Among these, in view of possibly increasing the capacity characteristics and stability of the battery, the lithium composite metal oxide may be $LiCoO_2$, $LiMnO_2$, $LiNiO_2$, a lithium-nickel-manganese-cobalt-based oxide (e.g., $Li(Ni_{0.6}Mn_{0.2}Co_{0.2})O_2$, $Li(Ni_{0.5}Mn_{0.3}Co_{0.2})O_2$, $Li(Ni_{0.8}Mn_{0.1}Co_{0.1})O_2$ or the like), or a lithium-nickel-cobalt-aluminum-based oxide (e.g., $LiNi_{0.8}Co_{0.15}Al_{0.05}O_2$ or the like). In consideration of the remarkableness of an improvement effect according to control of types and content ratios of components constituting the lithium composite metal oxide, the lithium composite metal oxide may be any one or a mixture of two or more of $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, $Li(Ni_{0.8}Mn_{0.1}Co_{0.1})O_2$, and the like.

The positive electrode active material may be included at 80 wt % to 99 wt % based on the total weight of the positive electrode slurry.

The conductive material is commonly added at 1 to 30 wt % based on the total weight of the positive electrode slurry.

Such a conductive material is not particularly limited as long as it does not cause a chemical change in the battery and has conductivity. For example, the conductive material may be graphite; a carbon-based material such as carbon black, acetylene black, Ketjen black, channel black, furnace black, lamp black, thermal black, or the like; a conductive fiber such as carbon fiber, metallic fiber, or the like; metallic powder such as carbon fluoride powder, aluminum powder, nickel powder, or the like; a conductive whisker such as zinc oxide, potassium titanate, or the like; a conductive metal oxide such as titanium oxide or the like; or a conductive material such as a polyphenylene derivative or the like. Specific examples of a commercially available conductive material include the acetylene black series (commercially available from Chevron Chemical Company), Denka black (Denka Singapore Private Limited or Gulf Oil Company products), Ketjen black, the EC series (commercially available from Armak Company), Vulcan XC-72 (commercially available from Cabot Company), and Super P (commercially available from Timcal).

The binder is a component that assists binding between an active material and a conductive material and binding to a current collector, and is commonly added at 1 to 30 wt % based on the total weight of the positive electrode slurry. Such a binder is, for example, polyvinylidene fluoride (PVDF), polyvinyl alcohol, carboxymethyl cellulose (CMC), starches, hydroxypropyl cellulose, regenerated cellulose, polyvinyl pyrrolidone, tetrafluoroethylene, polyethylene, polypropylene, an ethylene-propylene-diene terpolymer (EPDM), a sulfonated EPDM, styrene-butadiene rubber, fluororubber, one of various copolymers thereof, or the like.

The solvent may be an organic solvent such as N-methyl-2-pyrrolidone (NMP) or the like, and may be used in an amount in which preferable viscosity is exhibited when the positive electrode active material and optionally a binder, a conductive material, and the like are included. For example, the solvent may be included in such a way that a solid concentration in a slurry including the positive electrode active material and optionally including a binder and a conductive material is 50 wt % to 95 wt %, preferably 70 wt % to 90 wt %.

In addition, the negative electrode may be manufactured by forming a negative electrode mixture layer on a negative electrode current collector.

The negative electrode mixture layer may be formed by applying a slurry including a negative electrode active material, a binder, a conductive material, a solvent, and the like, followed by drying and rolling.

The negative electrode current collector generally has a thickness of 3 to 500 µm. Such a negative electrode current collector is not particularly limited as long as it does not cause a chemical change in the battery and has high conductivity. For example, copper, stainless steel, aluminum, nickel, titanium, calcined carbon, copper or stainless steel whose surface is treated with carbon, nickel, titanium, silver, or the like, an aluminum-cadmium alloy, or the like may be used as the negative electrode current collector. Also, the negative electrode current collector, like the positive electrode current collector, may have fine irregularities at a surface thereof to increase adhesion of the negative electrode active material. In addition, the negative electrode current collector may be used in any of various forms such as a film, a sheet, a foil, a net, a porous material, a foam, a non-woven fabric, and the like.

The negative electrode active material may be one or two or more selected from the group consisting of natural graphite, artificial graphite, or a carbon material; lithium-containing titanium composite oxide (LTO); a metal (Me) such as Si, Sn, Li, Zn, Mg, Cd, Ce, Ni, or Fe, or an alloy composed of the metal (Me); an oxide of the metal; and a composite of the metal and carbon.

The negative electrode active material may be included at 80 wt % to 99 wt % based on the total weight of the negative electrode slurry.

The binder is a component that assists binding between a conductive material, an active material, and a current collector, and is commonly added at 1 to 30 wt % based on the total weight of the negative electrode slurry. Such a binder is, for example, polyvinylidene fluoride (PVDF), polyvinyl alcohol, carboxymethyl cellulose (CMC), starches, hydroxypropyl cellulose, regenerated cellulose, polyvinyl pyrrolidone, tetrafluoroethylene, polyethylene, polypropylene, an ethylene-propylene-diene polymer (EPDM), a sulfonated EPDM, styrene-butadiene rubber, fluororubber, one of various copolymers thereof, or the like.

The conductive material is a component for further improving the conductivity of the negative electrode active material and may be added at 1 to 20 wt % based on the total weight of the negative electrode slurry. Such a conductive material is not particularly limited as long as it does not cause a chemical change in the battery and has conductivity. For example, graphite such as natural graphite, artificial graphite, or the like; carbon black such as acetylene black, Ketjen black, channel black, furnace black, lamp black, thermal black, or the like; a conductive fiber such as carbon fiber, metallic fiber, or the like; metallic powder such as carbon fluoride powder, aluminum powder, nickel powder, or the like; a conductive whisker such as zinc oxide, potassium titanate, or the like; a conductive metal oxide such as titanium oxide, or the like; or a conductive material such as a polyphenylene derivative or the like may be used as the conductive material.

The solvent may be water or an organic solvent such as NMP, alcohol or the like, and may be used in an amount in which preferable viscosity is exhibited when the negative electrode active material and optionally a binder, a conductive material, and the like are included. For example, the solvent may be included in such a way that a solid concentration in a slurry including the negative electrode active material and optionally including a binder and a conductive material is 50 wt % to 95 wt %, preferably 70 wt % to 90 wt %.

In addition, the separator may be a common porous polymer film conventionally used as a separator, for example a porous polymer film made of a polyolefin-based polymer such as an ethylene homopolymer, a propylene homopolymer, an ethylene/butene copolymer, an ethylene/hexene copolymer, an ethylene/methacrylate copolymer, or the like, or a stacked structure having two or more layers made thereof. Alternatively, the separator may be a common porous non-woven fabric, for example a non-woven fabric made of high-melting point glass fiber, polyethylene terephthalate fiber, or the like, but the present invention is not limited thereto.

The appearance of the lithium secondary battery according to the present invention is not particularly limited, but it may be a cylindrical form using a can, a prismatic form, a pouch form, or a coin form.

BEST MODE

Hereinafter, the present invention will be described in detail with reference to embodiments. However, embodiments of the present invention may be modified in several different forms, and the scope of the present invention is not limited to the embodiments to be described below. The embodiments of the present invention are provided so that this disclosure will be thorough and complete, and will fully convey the concept of embodiments to those skilled in the art.

EXAMPLES

Example 1

(Preparation of Non-Aqueous Electrolyte)

1 M $LiPF_6$ was dissolved in a mixed organic solvent in which ethylene carbonate (EC), propylene carbonate (PC), and ethyl methyl carbonate (EMC) were mixed (20:10:70 vol %), and then a compound of Formula I-1 was added at a content listed in Table 1 below to prepare a non-aqueous electrolyte.

(Manufacture of Positive Electrode)

A lithium cobalt composite oxide ($LiCO_2$) as a positive electrode active material particle, carbon black as a conductive material, and polyvinylidene fluoride (PVDF) as a binder were added in a weight ratio of 90:5:5 (wt %) to N-methyl-2-pyrrolidone (NMP) as a solvent in a weight ratio of 100:40 to prepare a positive electrode active material slurry. The positive electrode active material slurry was applied on a positive electrode current collector (Al thin film) having a thickness of 100 μm, dried, and roll-pressed to manufacture a positive electrode.

(Manufacture of Negative Electrode)

Natural graphite as a negative electrode active material, PVDF as a binder, and carbon black as a conductive material were added in a weight ratio of 95:2:3 (wt %) to NMP as a solvent in a weight ratio of 100:100 to prepare a negative electrode active material slurry. The negative electrode active material slurry was applied on a negative electrode current collector (Cu thin film) having a thickness of 90 μm, dried, and roll-pressed to manufacture a negative electrode.

(Manufacture of Secondary Battery)

The positive electrode and the negative electrode manufactured by the above-described methods were laminated together with a porous polyethylene film to manufacture an electrode assembly. Afterward, the electrode assembly thus manufactured was put into a battery case, and the above-prepared non-aqueous electrolyte was injected into the battery case and sealed to manufacture a lithium secondary battery.

Examples 2 to 28

Each of non-aqueous electrolytes and secondary batteries including the same according to Examples 2 to 28 was manufactured in the same manner as in Example 1 except that each additive was included at a content listed in Table 1 below when a non-aqueous electrolyte was prepared in Example 1.

Example 29

(Preparation of Non-Aqueous Electrolyte)

1 M $LiPF_6$ was dissolved in a mixed organic solvent in which ethylene carbonate (EC), propylene carbonate (PC), and ethyl methyl carbonate (EMC) were mixed (20:10:70 vol%), and then a compound of Formula I-1 was added at a content listed in Table 2 below to prepare a non-aqueous electrolyte.

(Manufacture of Positive Electrode)

A lithium cobalt composite oxide ($LiCO_2$) as a positive electrode active material particle, carbon black as a conductive material, and polyvinylidene fluoride (PVDF) as a binder were added in a weight ratio of 90:5:5 (wt %) to N-methyl-2-pyrrolidone (NMP) as a solvent in a weight ratio of 100:40 to prepare a positive electrode active material slurry. The positive electrode active material slurry was applied on a positive electrode current collector (Al thin film) having a thickness of 100 μm, dried, and roll-pressed to manufacture a positive electrode.

(Manufacture of Secondary Battery)

The positive electrode thus manufactured was punched to be used for a coin-type battery, and three iron (Fe) powders having an average particle size (D50) of about 200 pm were fixed on a surface of the positive electrode. Afterward, the non-aqueous electrolyte was injected to manufacture a coin-type half-secondary battery.

Examples 30 to 56

Each of non-aqueous electrolytes and secondary batteries including the same according to Examples 30 to 56 was manufactured in the same manner as in Example 29 except that each additive was included at a content listed in Table 2 below when a non-aqueous electrolyte was prepared in Example 29.

Comparative Example 1

A non-aqueous electrolyte and a secondary battery including the same were manufactured in the same manner as in Example 1 except that an additive was not included when a non-aqueous electrolyte was prepared in Example 1.

Comparative Example 2

As shown in Table 1 below, a non-aqueous electrolyte and a secondary battery including the same were manufactured in the same manner as in Example 1 except that 0.3 g of a compound of Formula a below was included instead of a compound of Formula I-1 when a non-aqueous electrolyte was prepared in Example 1.

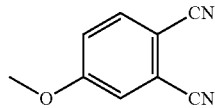

[Formula a]

Comparative Example 3

As shown in Table 1 below, a non-aqueous electrolyte and a secondary battery including the same were manufactured in the same manner as in Comparative Example 2 except that 0.5 g of a compound of Formula a was included when a non-aqueous electrolyte was prepared in Comparative Example 2.

Comparative Example 4

As shown in Table 1 below, a non-aqueous electrolyte and a secondary battery including the same were manufactured in the same manner as in Comparative Example 2 except that 7 g of a compound of Formula a was included when a non-aqueous electrolyte was prepared in Comparative Example 2.

Comparative Example 5

As shown in Table 1 below, a non-aqueous electrolyte and a secondary battery including the same were manufactured in the same manner as in Comparative Example 2 except that 0.5 g of a compound of Formula b below was included when a non-aqueous electrolyte was prepared in Comparative Example 2.

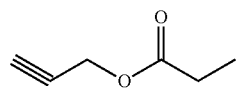

[Formula b]

Comparative Example 6

As shown in Table 1 below, a non-aqueous electrolyte and a secondary battery including the same were manufactured in the same manner as in Comparative Example 2 except that 0.3 g of a compound of Formula c below was included when a non-aqueous electrolyte was prepared in Comparative Example 2.

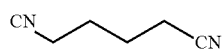

[Formula c]

Comparative Example 7

As shown in Table 1 below, a non-aqueous electrolyte and a secondary battery including the same were manufactured in the same manner as in Comparative Example 2 except that 0.5 g of a compound of Formula c was included when a non-aqueous electrolyte was prepared in Comparative Example 2.

Comparative Example 8

As shown in Table 1 below, a non-aqueous electrolyte and a secondary battery including the same were manufactured in the same manner as in Comparative Example 2 except that 7 g of a compound of Formula c was included when a non-aqueous electrolyte was prepared in Comparative Example 2.

Comparative Example 9

As shown in Table 1 below, a non-aqueous electrolyte and a secondary battery including the same were manufactured in the same manner as in Comparative Example 2 except that 0.5 g of a compound of Formula d below was included when a non-aqueous electrolyte was prepared in Comparative Example 2.

[Formula d]

Comparative Example 10

A non-aqueous electrolyte and a coin-type half-secondary battery including the same were manufactured in the same manner as in Example 29 except that an additive was not included when a non-aqueous electrolyte was prepared in Example 29.

Comparative Example 11

As shown in Table 2 below, a non-aqueous electrolyte and a coin-type half-secondary battery including the same were manufactured in the same manner as in Comparative Example 10 except that 0.3 g of a compound of Formula a was included when a non-aqueous electrolyte was prepared in Comparative Example 10.

Comparative Example 12

As shown in Table 2 below, a non-aqueous electrolyte and a coin-type half-secondary battery including the same were manufactured in the same manner as in Comparative Example 10 except that 0.5 g of a compound of Formula a was included when a non-aqueous electrolyte was prepared in Comparative Example 10.

Comparative Example 13

As shown in Table 2 below, a non-aqueous electrolyte and a coin-type half-secondary battery including the same were manufactured in the same manner as in Comparative Example 10 except that 7 g of a compound of Formula a was included when a non-aqueous electrolyte was prepared in Comparative Example 10.

Comparative Example 14

As shown in Table 2 below, a non-aqueous electrolyte and a coin-type half-secondary battery including the same were manufactured in the same manner as in Comparative Example 10 except that 0.5 g of a compound of Formula b was included when a non-aqueous electrolyte was prepared in Comparative Example 10.

Comparative Example 15

As shown in Table 2 below, a non-aqueous electrolyte and a coin-type half-secondary battery including the same were manufactured in the same manner as in Comparative Example 10 except that 0.3 g of a compound of Formula c was included when a non-aqueous electrolyte was prepared in Comparative Example 10.

Comparative Example 16

As shown in Table 2 below, a non-aqueous electrolyte and a coin-type half-secondary battery including the same were manufactured in the same manner as in Comparative Example 10 except that 0.5 g of a compound of Formula c was included when a non-aqueous electrolyte was prepared in Comparative Example 10.

Comparative Example 17

As shown in Table 2 below, a non-aqueous electrolyte and a coin-type half-secondary battery including the same were manufactured in the same manner as in Comparative Example 10 except that 7 g of a compound of Formula c was included.

Comparative Example 18

As shown in Table 2 below, a non-aqueous electrolyte and a coin-type half-secondary battery including the same were manufactured in the same manner as in Comparative Example 10 except that 0.5 g of a compound of Formula d was included.

EXPERIMENTAL EXAMPLES

Experimental Example 1

Each of the secondary batteries according to Examples 1 to 28 and Comparative Examples 1 to 9 was charged at a rate of 0.8 C until 4.35V under constant current(CC)/constant voltage(CV) conditions, cut off at 0.05 C, and discharged at 0.5 C until 3.0V (initial discharge capacity). Subsequently, the secondary battery was charged at a rate of 0.8 C until 4.35V under CC/CV conditions, cut off at 0.05 C, and then stored at 60° C. for 2 weeks. Afterward, the secondary battery was discharged at 0.5 C until 3.0V at room temperature, and then discharge capacity thereof was measured (residual discharge capacity). The secondary battery was charged again at a rate of 0.8 C until 4.35V under CC/CV conditions, cut off at 0.05 C, and then discharged at 0.5 C until 3.0V. Afterward, discharge capacity thereof was measured (recovery discharge capacity).

The residual discharge capacity and recovery discharge capacity with respect to initial discharge capacity were calculated as a percentage, and these are shown in Table 1 below.

Experimental Example 2

Each of the secondary batteries according to Examples 1 to 28 and Comparative Examples 1 to 9 was charged at a rate of 0.8 C until 4.35V under constant current(CC)/constant voltage(CV) conditions, cut off at 0.05 C, and discharged at 0.5 C until 3.0V. Subsequently, the secondary battery was charged at a rate of 0.8 C until 4.35V under CC/CV conditions, cut off at 0.05 C, and discharged at 0.5 C until 3.0V at room temperature. This process was determined as one cycle and repeated for 200 cycles. Afterward, cycle capacity retention with respect to one cycle capacity was calculated as a percentage, and these are shown in Table 1 below.

TABLE 1

| Example | Content of non-aqueous organic solvent (g) | Additive Formula | Additive Content (g) | Residual discharge capacity (%) | Recovery discharge capacity (%) | Cycle capacity retention (%) |
|---|---|---|---|---|---|---|
| Example 1 | 99.5 | I-1 | 0.5 | 85 | 95 | 91 |
| Example 2 | 99.5 | I-2 | 0.5 | 83 | 96 | 90 |
| Example 3 | 99.5 | I-3 | 0.5 | 80 | 94 | 88 |
| Example 4 | 99.5 | I-5 | 0.5 | 87 | 93 | 90 |
| Example 5 | 99.5 | I-6 | 0.5 | 85 | 94 | 93 |
| Example 6 | 99.5 | I-9 | 0.5 | 83 | 95 | 89 |
| Example 7 | 99.5 | I-10 | 0.5 | 81 | 95 | 90 |
| Example 8 | 99.5 | I-12 | 0.5 | 84 | 93 | 91 |
| Example 9 | 99.5 | I-13 | 0.5 | 85 | 96 | 92 |
| Example 10 | 99.5 | I-14 | 0.5 | 83 | 94 | 88 |
| Example 11 | 99.5 | I-15 | 0.5 | 85 | 94 | 93 |
| Example 12 | 99.5 | I-16 | 0.5 | 81 | 92 | 93 |
| Example 13 | 99.5 | I-37 | 0.5 | 82 | 93 | 89 |
| Example 14 | 99.5 | I-39 | 0.5 | 82 | 95 | 87 |
| Example 15 | 99 | I-5 | 1 | 90 | 96 | 93 |
| Example 16 | 95 | I-5 | 5 | 89 | 94 | 88 |
| Example 17 | 99.5 | I-24 | 0.5 | 84 | 93 | 89 |
| Example 18 | 99.5 | I-25 | 0.5 | 81 | 95 | 91 |
| Example 19 | 99.5 | I-26 | 0.5 | 80 | 93 | 89 |
| Example 20 | 99.5 | I-28 | 0.5 | 85 | 93 | 92 |
| Example 21 | 99.5 | I-29 | 0.5 | 85 | 95 | 94 |
| Example 22 | 99.5 | II-1 | 0.5 | 81 | 92 | 90 |
| Example 23 | 99.5 | II-3 | 0.5 | 82 | 92 | 92 |
| Example 24 | 99.5 | II-4 | 0.5 | 84 | 95 | 93 |
| Example 25 | 99.5 | I-35 | 0.5 | 82 | 92 | 92 |
| Example 26 | 99.5 | I-36 | 0.5 | 84 | 93 | 90 |
| Example 27 | 95 | I-24 | 5 | 91 | 97 | 95 |
| Example 28 | 99 | I-24 | 1 | 88 | 95 | 92 |
| Comparative Example 1 | 100 | X | X | 64 | 80 | 60 |
| Comparative Example 2 | 99.7 | a | 0.3 | 80 | 87 | 65 |
| Comparative Example 3 | 99.5 | a | 0.5 | 70 | 80 | 65 |
| Comparative Example 4 | 93 | a | 7 | 76 | 85 | 70 |
| Comparative Example 5 | 99.5 | b | 0.5 | 72 | 83 | 70 |
| Comparative Example 6 | 99.7 | c | 0.3 | 69 | 84 | 71 |
| Comparative Example 7 | 99.5 | c | 0.5 | 73 | 84 | 69 |
| Comparative Example 8 | 93 | c | 7 | 76 | 85 | 70 |
| Comparative Example 9 | 99.5 | d | 0.5 | 67 | 82 | 64 |

As shown in Table 1, it can be seen that the secondary batteries according to Examples 1 to 28, in which the non-aqueous electrolyte including a compound containing a nitrile group and a propargyl group as an additive according to the present invention was included, had a residual discharge capacity of about 80% or more, a recovery discharge capacity of about 92% or more, and a cycle capacity retention of about 87% or more when stored at high temperature, all of which are excellent.

On the other hand, it can be confirmed that the secondary battery according to Comparative Example 1, in which an additive was not used, had a residual discharge capacity of about 64%, a recovery discharge capacity of about 80%, and a cycle capacity retention of about 60% when stored at high temperature, which indicates that performance in various aspects was degraded compared to the secondary batteries according to Examples 1 to 28.

In addition, it can be confirmed that the secondary batteries according to Comparative Examples 2 to 9, in which compounds of Formulas a to d were included as a non-aqueous electrolyte additive, had a residual discharge capacity of about 80% or less, a recovery discharge capacity of about 87% or less, and a cycle capacity retention of about 70% or less when stored at high temperature, all of which are less than those of the secondary batteries according to Examples 1 to 28.

Experimental Example 3

Each of the coin-type half-secondary batteries according to Examples 29 to 56 and Comparative Examples 10 to 18 was charged at a rate of 0.8 C until 4.35V under CC/CV conditions, cut off at 0.05 C, and discharged at 0.5 C until 3.0V. In each example, five batteries were manufactured, and the number of batteries capable of charging and discharging was counted, the results of which are shown in Table 2 below.

In addition, the batteries capable of charging and discharging were charged at a rate of 0.8 C until 4.35V under CC/CV conditions, and then stored at 45° C. for 6 days. After storage, voltage was measured at 45° C., the results of which are shown in Table 2 below.

TABLE 2

| | Content of non-aqueous organic solvent (g) | Additive Formula | Content (g) | Number of battery capable of charging discharging (Possibility/ Manufacture) | Voltage after and storage at high temperature (V) |
|---|---|---|---|---|---|
| Example 29 | 99.5 | I-1 | 0.5 | 4/5 | 4.13 |
| Example 30 | 99.5 | I-2 | 0.5 | 4/5 | 4.05 |
| Example 31 | 99.5 | I-3 | 0.5 | 4/5 | 4.10 |
| Example 32 | 99.5 | I-5 | 0.5 | 4/5 | 4.12 |
| Example 33 | 99.5 | I-6 | 0.5 | 3/5 | 4.16 |
| Example 34 | 99.5 | I-9 | 0.5 | 3/5 | 4.02 |
| Example 35 | 99.5 | I-10 | 0.5 | 4/5 | 4.08 |
| Example 36 | 99.5 | I-12 | 0.5 | 4/5 | 4.10 |
| Example 37 | 99.5 | I-13 | 0.5 | 4/5 | 4.01 |
| Example 38 | 99.5 | I-14 | 0.5 | 4/5 | 4.05 |
| Example 39 | 99.5 | I-15 | 0.5 | 4/5 | 4.03 |
| Example 40 | 99.5 | I-16 | 0.5 | 5/5 | 4.09 |
| Example 41 | 99.5 | I-37 | 0.5 | 5/5 | 4.22 |
| Example 42 | 99.5 | I-39 | 0.5 | 5/5 | 4.17 |
| Example 43 | 99 | I-5 | 1 | 5/5 | 4.19 |
| Example 44 | 95 | I-5 | 5 | 5/5 | 4.26 |
| Example 45 | 99.5 | I-24 | 0.5 | 5/5 | 4.20 |
| Example 46 | 99.5 | I-25 | 0.5 | 4/5 | 4.02 |
| Example 47 | 99.5 | I-26 | 0.5 | 4/5 | 4.11 |
| Example 48 | 99.5 | I-28 | 0.5 | 4/5 | 4.16 |
| Example 49 | 99.5 | I-29 | 0.5 | 3/5 | 4.10 |
| Example 50 | 99.5 | II-1 | 0.5 | 5/5 | 4.18 |
| Example 51 | 99.5 | II-3 | 0.5 | 4/5 | 4.06 |
| Example 52 | 99.5 | II-4 | 0.5 | 4/5 | 4.10 |
| Example 53 | 99.5 | I-35 | 0.5 | 4/5 | 4.04 |
| Example 54 | 99.5 | I-36 | 0.5 | 4/5 | 4.01 |
| Example 55 | 95 | I-24 | 5 | 4/5 | 4.02 |
| Example 56 | 99 | I-24 | 1 | 5/5 | 4.15 |
| Comparative Example 10 | 100 | X | X | 0/5 | 2.65 |
| Comparative Example 11 | 99.7 | a | 0.3 | 1/5 | 3.45 |
| Comparative Example 12 | 99.5 | a | 0.5 | 3/5 | 3.67 |
| Comparative Example 13 | 93 | a | 7 | 5/5 | 3.93 |
| Comparative Example 14 | 99.5 | b | 0.5 | 3/5 | 3.55 |
| Comparative Example 15 | 99.7 | c | 0.3 | 1/5 | 3.55 |
| Comparative Example 16 | 99.5 | c | 0.5 | 3/5 | 3.87 |
| Comparative Example 17 | 93 | c | 7 | 5/5 | 3.93 |
| Comparative Example 18 | 99.5 | d | 0.5 | 1/5 | 3.34 |

As shown in Table 2, it can be seen that the secondary batteries according to Examples 29 to 56 were capable of charging and discharging in most cases, and maintained a voltage of about 4.01V or more even when stored at high temperature because a compound containing a nitrile group and a propargyl group included as an additive formed a complex through combination with Fe impurities to suppress elution of metal ions.

On the other hand, it can be seen that the secondary battery according to Comparative Example 10, in which an additive was not used, was not capable of charging and discharging in most cases, and voltage after storage at high temperature was also reduced to 2.65 V.

In addition, it can be confirmed that the secondary batteries according to Comparative Examples 11, 12, 14, 15, 16, and 18, in which compounds of Formulas a to d were included as a non-aqueous electrolyte additive, were capable of charging and discharging in some cases, but voltage after storage at high temperature was reduced to less than 3.7 V.

Meanwhile, it can be confirmed that the secondary batteries according to Comparative Examples 13 and 17 exhibited a higher number of batteries capable of charging and discharging and a higher voltage after storage at high temperature than the secondary batteries according to Comparative Examples 11, 12, 14, 15, 16, and 18 because an excessive amount of an additive capable of suppressing elution of metal ions was included, but voltage after storage at high temperature was lower than that of the secondary batteries according to Examples 29 to 56 due to an increase in resistance.

The invention claimed is:

1. A non-aqueous electrolyte additive comprising at least one compound selected from the group consisting of compounds represented by Formula I and Formula II below:

[Formula I]

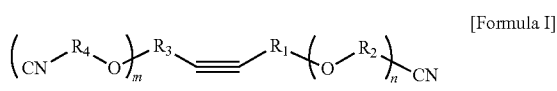

wherein R₁ is a $C_1$ to $C_5$ linear or nonlinear alkylene group substituted or unsubstituted with at least one nitrile group, or a $C_6$ to $C_8$ aromatic group substituted or unsubstituted with at least one nitrile group, R₂ is a $C_1$ to $C_5$ linear or nonlinear alkylene group substituted or unsubstituted with at least one nitrile group, a $C_6$ to $C_8$ aromatic group substituted or unsubstituted with at least one nitrile group, a $C_6$ to $C_8$ heteroaromatic group substituted or unsubstituted with at least one nitrile group, a $C_2$ to $C_5$ linear or nonlinear alkenyl group, or —C(O)—R₉—, wherein R₉ is a $C_1$ to $C_3$ linear or nonlinear alkylene group substituted with at least one nitrile group, R₃ is hydrogen or a $C_1$ to $C_5$ linear or nonlinear unsubstituted alkyl group when m is 0, and a $C_1$ to $C_5$ linear or nonlinear alkylene group when m is 1, R₄ is a $C_1$ to $C_3$ alkylene group or —R₁₀—C(O)—, wherein R₁₀ is a $C_1$ to $C_3$ alkylene group, and n and m each independently are an integer of 0 or 1,

[Formula II]

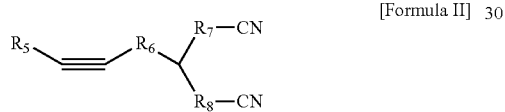

wherein R₅ is hydrogen or a $C_1$ to $C_5$ linear or nonlinear alkyl group substituted or unsubstituted with at least one nitrile group, wherein R₆ is a $C_1$ to $C_5$ linear or nonlinear alkylene group, and wherein R₇ to R₈ each independently are a $C_1$, $C_3$, $C_4$, or $C_5$ linear or nonlinear alkylene group.

2. The non-aqueous electrolyte additive of claim 1, wherein the non-aqueous electrolyte additive comprises at least one compound selected from the group consisting of compounds represented by Formulae I-1 to I-9 and I-11 to I-23, and I-25 to I-39 below:

(Formula I-1)

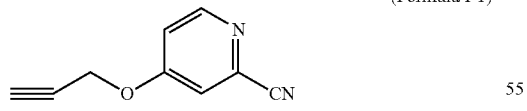

(Formula I-2)

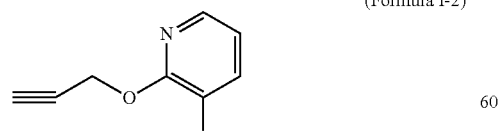

(Formula I-3)

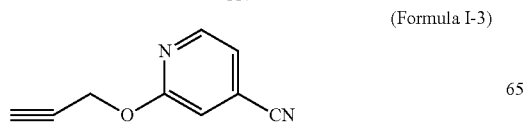

(Formula I-4)

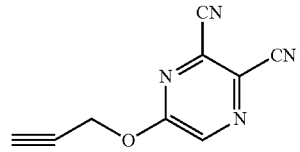

(Formula I-5)

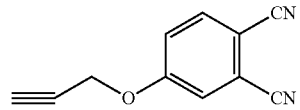

(Formula I-6)

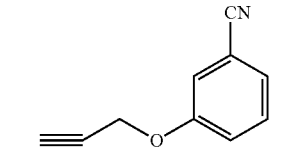

(Formula I-7)

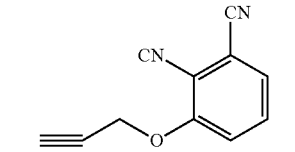

(Formula I-8)

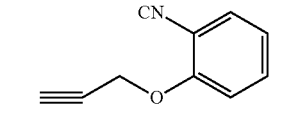

(Formula I-9)

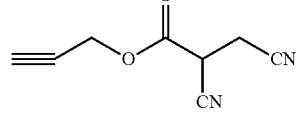

(Formula I-11)

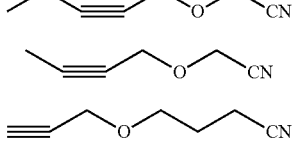

(Formula I-12)

(Formula I-13)

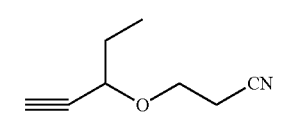

(Formula I-14)

(Formula I-15)

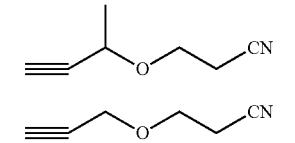

(Formula I-16)

(Formula I-17)

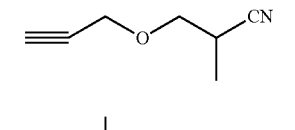

(Formula I-18)

(Formula I-19)

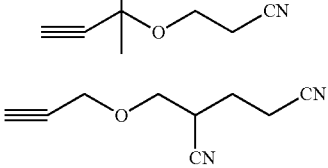

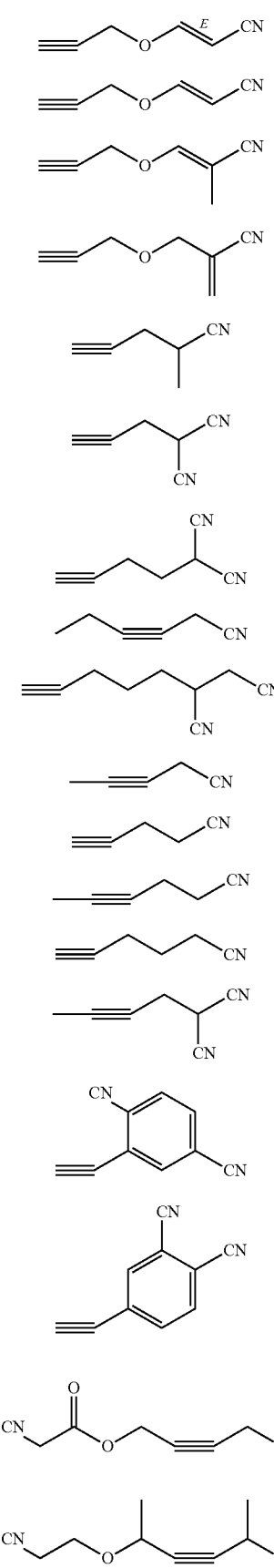

(Formula I-20)
(Formula I-21)
(Formula I-22)
(Formula I-23)
(Formula I-25)
(Formula I-26)
(Formula I-27)
(Formula I-28)
(Formula I-29)
(Formula I-30)
(Formula I-31)
(Formula I-32)
(Formula I-33)
(Formula I-34)
(Formula I-35)
(Formula I-36)
(Formula I-37)
(Formula I-38)

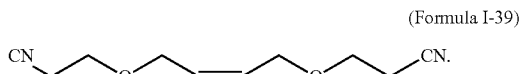
(Formula I-39)

3. The non-aqueous electrolyte additive of claim 1, wherein the non-aqueous electrolyte additive comprises at least one compound selected from the group consisting of compounds represented by Formula II-1 to Formula II 3 below:

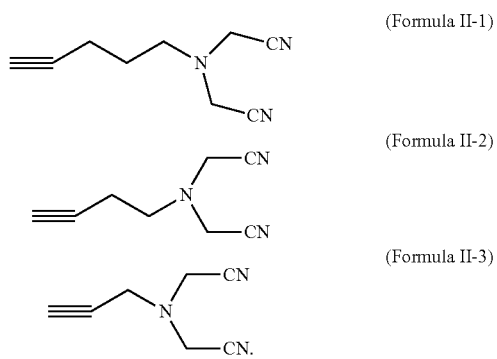
(Formula II-1)
(Formula II-2)
(Formula II-3)

4. A non-aqueous electrolyte for a lithium secondary battery comprising:
   an ionizable lithium salt;
   an organic solvent; and
   a non-aqueous electrolyte additive,
   wherein the non-aqueous electrolyte additive includes at least one compound selected from the group consisting of compounds represented by Formula I and Formula II below:

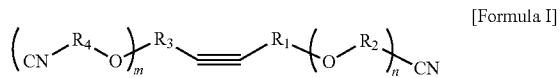
[Formula I]

wherein $R_1$ is a $C_1$ to $C_5$ linear or nonlinear alkylene group substituted or unsubstituted with at least one nitrile group, or a $C_6$ to $C_8$ aromatic group substituted or unsubstituted with at least one nitrile group, $R_2$ is a $C_1$ to $C_5$ linear or nonlinear alkylene group substituted or unsubstituted with at least one nitrile group, a $C_6$ to $C_8$ aromatic group substituted or unsubstituted with at least one nitrile group, a $C_6$ to $C_8$ heteroaromatic group substituted or unsubstituted with at least one nitrile group, a $C_2$ to $C_5$ linear or nonlinear alkenyl group, or —C(O)—$R_9$—, wherein $R_9$ is a $C_1$ to C3 linear or nonlinear alkylene group substituted with at least one nitrile group, $R_3$ is hydrogen or a $C_1$ to $C_5$ linear or nonlinear unsubstituted alkyl group when m is 0, and a $C_1$ to $C_5$ linear or nonlinear alkylene group when m is 1, $R_4$ is a $C_1$ to $C_3$ alkylene group or —$R_{10}$—C(O)—, wherein $R_{10}$ is a $C_1$ to $C_3$ alkylene group, and n and m each independently are an integer of 0 or 1,

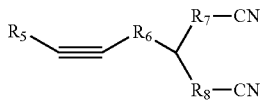
[Formula II]

wherein $R_5$ is hydrogen or a $C_1$ to $C_5$ linear or nonlinear alkyl group substituted or unsubstituted with at least one nitrile group, wherein $R_6$ is a $C_1$ to $C_5$ linear or nonlinear alkylene group, and wherein $R_7$ to $R_8$ each independently are a $C_1$, $C_3$, $C_4$, or $C_5$ linear or nonlinear alkylene group.

5. The non-aqueous electrolyte of claim 4, wherein the non-aqueous electrolyte additive is included at 0.5 wt % to 5 wt % based on a total content of the non-aqueous electrolyte.

6. The non-aqueous electrolyte of claim 5, wherein the non-aqueous electrolyte additive is included at 1 wt % to 5 wt % based on a total content of the non-aqueous electrolyte.

7. The non-aqueous electrolyte of claim 4, wherein the lithium salt includes $Li^+$ as a cation and any one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(F_2SO_2)_2N^-$, $CF_3CF_2(CF_3)_2CO^-$, $(CF_3SO_2)_2CH^-$, $CF_3(CF_2)_7SO_3^-$, $CF_3CO_2^-$, $CH_3CO_2^-$, $SCN^-$, and $(CF_3CF_2SO_2)_2N^-$ as an anion.

8. The non-aqueous electrolyte of claim 4, wherein the organic solvent includes a mixture of at least one selected from the group consisting of an ether, an ester, an amide, a linear carbonate, and a cyclic carbonate.

9. A lithium secondary battery comprising a negative electrode, a positive electrode, a separator interposed between the negative electrode and the positive electrode, and a non-aqueous electrolyte, wherein the non-aqueous electrolyte is the non-aqueous electrolyte for a lithium secondary battery according to claim 4.

* * * * *